United States Patent [19]

Nachbur et al.

[11] 3,932,502

[45] Jan. 13, 1976

[54] PROCESS FOR THE MANUFACTURE OF PHOSPHORUS-CONTAINING CONDENSATION PRODUCTS, THE PRODUCTS AND THEIR USE AS FLAMEPROOFING AGENTS

[75] Inventors: Hermann Nachbur, Dornach; Arthur Maeder, Therwil, both of Switzerland

[73] Assignee: Ciba-Geigy Corporation, Ardsley, N.Y.

[22] Filed: Aug. 31, 1972

[21] Appl. No.: 285,172

[30] Foreign Application Priority Data

Jan. 14, 1972 Switzerland............................ 518/72

[52] U.S. Cl........... 260/553 B; 260/2 P; 260/552 R; 252/8.1; 428/276
[51] Int. Cl.$^2$......................................... C07C 127/24
[58] Field of Search............ 260/553 E, 553 R, 2 P, 260/557 B

[56] References Cited
FOREIGN PATENTS OR APPLICATIONS
761,985 11/1956 United Kingdom
906,314 9/1962 United Kingdom................ 260/2 P Primary Examiner—James O. Thomas, Jr.
Assistant Examiner—G. Breitenstein
Attorney, Agent, or Firm—Joseph G. Kolodny; Prabodh I. Almaula; Edward McC. Roberts

[57] ABSTRACT

The subject of the invention is a process for the manufacture of water-soluble condensation products of hydroxymethylphosphonium compounds and thiourea or biuret, characterised in that (a) one mol of a tetrakis-(hydroxymethyl)-phosphonium compound is condensed with (b) 0.02 to 0.5 mol, preferably 0.1 to 0.3 mol, of optionally methylolated thiourea or biuret at 40° to 120°C, optionally in the presence of formaldehyde or a formaldehyde-releasing agent and optionally in the presence of an inert organic solvent, the condensation is optionally thereafter continued at temperatures of 100° to 150°C and, if appropriate, free hydroxyl groups are etherified at least partially with at least one alkanol with 1 to 4 carbon atoms and, if appropriate, the salts of the condensation products are converted into the corresponding hydroxides. In addition to the preferred molar ratio range of 1:0.1 to 0.3, the range of 0.2 to 0.5 is also advantageous.

The condensation products are used for flameproofing organic fibre material, especially textiles.

12 Claims, No Drawings

PROCESS FOR THE MANUFACTURE OF PHOSPHORUS-CONTAINING CONDENSATION PRODUCTS, THE PRODUCTS AND THEIR USE AS FLAMEPROOFING AGENTS

The subject of the invention is a process for the manufacture of water-soluble condensation products of hydroxymethylphosphonium compounds and thiourea or biuret, characterised in that (a) one mol of a tetrakis-(hydroxymethyl)-phosphonium compound is condensed with (b) 0.02 to 0.5 mol, preferably 0.1 to 0.3 mol, of optionally methylolated thiourea or biuret at 40° to 120°C, optionally in the presence of formaldehyde or a formaldehyde-releasing agent and optionally in the presence of an inert organic solvent, the condensation is optionally thereafter continued at temperatures of 100° to 150°C and, if appropriate, free hydroxyl groups are etherified at least partially with at least one alkanol with 1 to 4 carbon atoms and, if appropriate, the salts of the condensation products are converted into the corresponding hydroxides. In addition to the preferred molar ratio range of 1:0.1 to 0.3, the range of 0.2 to 0.5 is also advantageous.

The condensation is preferably carried out at 70° to 110°C in an inert organic solvent or solvent mixture. For this, aromatic hydrocarbons are above all suitable, such as, for example, toluene, o-, m- or p-xylene or a mixture thereof, or xylene-toluene, xylene-benzene or xylene-decahydronaphthalene mixtures. Preferably, the optional subsequent further condensation is carried out at 125° to 140°C or, in particular, at about 135°C, that is to say the boiling point of the solvent or solvent mixture; in the particular case where thiourea is used as the component (b), it is desirable to carry out a further condensation at 125° to 140°C.

At the same time it is however also possible to carry out the condensation in the absence of an inert organic solvent, for example by using already prepared condensation products as the solvent or by carrying out the condensation in the melt.

An appropriate procedure is to heat the tetrakis-(hydroxymethyl)-phosphonium compound, which as a rule is in the form of an aqueous solution, together with the component (b), optionally in a solvent, to the boil and to distil off the water. Possible tetrakis-(hydroxymethyl)-phosphonium compounds are above all salts and the hydroxide.

Amongst the tetrakis-(hydroxymethyl)-phosphonium salts used, the halides, such as, for example, the bromide or especially the chloride, are preferred. Tetrakis-(hydroxymethyl)-phosphonium chloride is hereafter referred to as THPC.

Where the tetrakis-(hydroxymethyl)-phosphonium hydroxide (THPOH) is used as the starting product, it is appropriately manufactured beforehand from a corresponding salt, for example THPC, by neutralisation, in aqueous solution, with a base, for example sodium hydroxide, followed by dehydration.

Thiourea or biuret can be used as such or in the methylolated form. The non-methylolated products are preferred.

The formaldehyde which is optionally used conjointly is preferably in the form of an aqueous solution. Possible formaldehyde-releasing agents are above all paraformaldehyde.

The etherification, which is optionally to be carried out, of the condensation product which still contains free hydroxyl groups is effected with, for example, n-butanol, n-propanol, ethanol or especially methanol. Preferably, this is done in an acid medium.

The acid catalysts optionally used conjointly in the condensation are preferably acid salts (LEWIS acids) such as magnesium chloride, iron-II chloride, zinc nitrate or boron trifluoride/diethyl ether. The conjoint use of these catalysts is particularly advisable in the case of the condensation with THPOH.

After completion of condensation and, if appropriate, etherification, the salts of the condensation products can also be completely or partially converted into their corresponding hydroxides, which as a rule is achieved by adding strong bases, such as alkali metal hydroxides or alkaline earth metal hydroxides, for example sodium hydroxide, potassium hydroxide or calcium hydroxide, and also sodium carbonate. The amount of base is appropriately so chosen that the pH value of the reaction mixture is about 5 to 8. This conversion is appropriately effected in the application bath.

At times, the end products have an unpleasant odour caused by volatile low molecular trivalent phosphorus compounds, for example phosphines, such as trihydroxymethylphosphine. This odour can be eliminated by an oxidative after-treatment of the condensation product, for example by passing air or oxygen into the reaction mixture or by adding oxidising agents, such as hydrogen peroxide or potassium persulphate.

The condensation products are used for flameproofing organic fibre material, especially textiles. An appropriate procedure for this is to treat these materials with an aqueous preparation which contains at least (1) a condensation product of the indicated nature and (2) a polyfunctional compound which differs from the condensation products according to (1), and to dry the materials treated in this way and finish them by the wet batch process, especially the moist batch process or ammonia process, or preferably by the thermofixing process.

The component (2) preferably consists of polyfunctional epoxides or above all of polyfunctional nitrogen compounds. Possible epoxides are above all epoxides which are liquid at room temperature and have at least two epoxide groups which are preferably derived from polyhydric phenols. Polyfunctional nitrogen compounds are, for example, polyalkylenepolyamines or, in particular, aminoplast-forming agents or aminoplast precondensates. The latter are preferred.

By aminoplast-forming agents there are understood nitrogen compounds which can be methylolated, and by aminoplast precondensates there are understood addition products of formaldehyde to nitrogen compounds which can be methylolated. As aminoplast-forming agents or nitrogen compounds which can be methylolated, there may be mentioned: 1,3,5-aminotriazines such as N-substituted melamines, for example N-butylmelamine, N-trihalogenomethylmelamines, triazones, and also ammeline, guanamines, for example benzoguanamines or acetoguanamines, or also diguanamines.

Further possibilities are: cyanamide, acrylamide, alkylureas or arylureas and alkylthioureas or arylthioureas, alkyleneureas or alkylenediureas, for example urea, thiourea, urones, ethyleneurea, propyleneurea, acetylenediurea or especially 4,5-dihydroxyimidazolidone-2 and derivatives thereof, for example 4,5-dihydroxyimidazolidone-2 substituted in the 4-position, at the hydroxyl group, by the —CH$_2$CH$_2$CO—NH—CH$_2$OH radical. The methylol compounds of a urea, of an ethyleneurea or of melamine are preferentially used. Valuable products are provided in general by products which are as highly methylolated as possible, but in particular also by products with low methylolation. Suitable aminoplast precondensates are both predominantly monomolecular aminoplasts and also more highly precondensed aminoplasts.

The ethers of these aminoplast precondensates can also be used together with the reaction products. For example, the ethers of alkanols such as methanol, ethanol, n-propanol, isopropanol, n-butanol or pentanols, are of advantage. It is however desirable that these aminoplast precondensates should be water-soluble, such as, for example, the pentamethylol-melamine-dimethyl-ether.

The organic fibre materials to be provided with a flameproof finish are, for example, wood, paper, furs, hides or, preferably, textiles. In particular, fibre materials of polyamides, cellulose, cellulose-polyester or polyester are flameproofed, with fabrics of wool or polyester or above all mixed fabrics of polyester and cellulose, wherein the ratio of the polyester constituent to the cellulose constituent is 1:4 to 2:1, being preferred. Thus, for example, so-called 20/80, 26/74, 50/50 or 67/33 polyester-cellulose mixed fabrics can be used.

The cellulose or the cellulose constituent of the fibre material originates, for example, from linen, cotton, rayon or staple viscose. In addition to polyester-cellulose fibre mixtures it is also possible to use fibre mixtures of cellulose with natural or synthetic polyamides. Above all, fibre materials of wool can also be flameproofed well with the polycondensation products.

The aqueous preparations for flameproofing the organic fibre materials as a rule contain 200 to 800 g/l, preferably 350 to 600 g/l, of the component (1) and 20 to 200 g/l, preferably 40 to 120 g/l, of the component (2). The preparations in most cases have an acid to neutral or weakly alkaline pH value.

The preparations for flameproofing can optionally contain yet further additives. To achieve a greater deposit of material on fabrics it is advantageous, for example, to add 0.1 to 0.5%o of a high molecular polyethylene glycol. Further, the customary plasticisers, for example an aqueous polyethylene emulsion or silicone oil emulsion, can be added to the preparations.

To improve the mechanical strengths of the fibres, suitable copolymers can also be added to the preparations, for example copolymers of N-methylolacrylamide or cationic copolymers. For example, aqueous emulsions of copolymers of (a) 0.25 to 10% of an alkaline earth metal salt of an $\alpha,\beta$-ethylenically unsaturated monocarboxylic acid, (b) 0.25 to 30% of a N-methylolamide or N-methylolamide-ether of an $\alpha,\beta$-ethylenically unsaturated monocarboxylic or dicarboxylic acid and (c) 99.5 to 60% of at least one other copolymerisable compound are advantageous in this context. These copolymers and their manufacture are known. The tenacity and abrasion resistance of the treated fibre material can be favourably influenced by the conjoint use of such a copolymer.

If a polymer of the indicated type is further added to the preparation, the amounts are advantageously small, for example 1 to 10%, relative to the amount of the condensation product. The same is true of any plasticiser, where the appropriate amounts can again be 1 to 10%.

It is also possible, though in most cases not necessary, to add curing catalysts such as, for example, ammonium chloride, ammonium dihydrogen orthophosphate, phosphoric acid, magnesium chloride or zinc nitrate. The pH value of the preparations is as a rule 2 to 7.5, preferably 4 to 7, and is adjusted in the usual manner by adding bases or acids.

It can also be advantageous to add buffer substances, for example sodium carbonate, disodium phosphate and trisodium phosphate and triethanolamine.

To improve the durability of the flameproof finishes and to achieve a soft handle, it can be advantageous to add to the aqueous preparations halogenated paraffins in combination with a polyvinyl halide compound.

The preparations are now applied to the fibre materials, and this can be done in a manner which is in itself known. Preferably, piece goods are used and impregnated on a padder which is charged with the preparation at room temperature.

In the preferred thermofixing process, the fibre material impregnated in this way must now be dried and subjected to a heat treatment. It is appropriately dried at temperatures of up to 100°C. Thereafter the material is subjected to a heat treatment at temperatures above 100°C, for example 100° to 200°C, preferably 120° to 180°C, the duration of which can be the shorter, the higher is the temperature. This duration of heating, is, for example, 30 seconds to 10 minutes.

If the moist fixing process is used, the fabric is first dried to a residual moisture content of about 5 to 20% and then batched for 12 to 48 hours at about 40° to 60°C, rinsed, washed and dried. In the wet fixing process, a similar procedure is followed except that the completely wet fibre material is batched. In the ammonia fixing process, the treated fibre material is first, in the moist state, gassed with ammonia and is subsequently dried.

A rinse with an acid-binding agent, preferably with aqueous sodium carbonate solution, can be desirable in the case of a strongly acid reaction medium.

The percentages and parts in the examples which follow are parts by weight or percentages by weight. The relationship of parts by volume to parts by weight is as of ml to g.

EXAMPLE 1

244 parts of a 78% strength aqueous THPC solution (1 mol of THPC), 19 parts of thiourea (0.25 mol) and 200 parts of a xylene isomer mixture are heated to the boil, with rapid stirring, in a stirred vessel of 500 parts by volume capacity which is equipped with a water separator and thermometer. At a boiling point of 105°C, the azeotropic removal of the water from the aqueous THPC solution starts. After removal of this water (53.3 parts) the boiling point of the xylene is 130°C. A further 26 parts of water are now removed azeotropically by additional treatment at 130°C, after which the condensation product forms a very highly viscous mass. The product is cooled to 90°C and dissolved by adding 200 parts of water, and the xylene is largely syphoned off. The aqueous solution is completely evaporated in vacuo at 70°C. 160 parts of a very highly viscous yellowish condensation product are obtained and this is diluted to 80% active substance content with water to facilitate handling.

The infrared spectrum of this product shows the following bands:

| | | | | |
|---|---|---|---|---|
| Broad | band at approx. | 3,240 | $cm^{-1}$ | strong |
| Broad shoulder | " | 2,980 | " | weak |
| Broad shoulder | " | 2,905 | " | weak |
| Broad shoulder | " | 2,850 | " | weak |
| Broad shoulder | " | 2,670 | " | weak |
| Broad shoulder | " | 2,480 | " | weak |
| Broad shoulder | " | 2,360 | " | weak |
| Broad shoulder | " | 2,080 | " | weak |
| Broad shoulder | " | 1,705 | " | medium |
| Broad | " | 1,635 | " | medium |
| Broad | " | 1,540 | " | weak |
| Broad shoulder | " | 1,455 | " | weak |
| Broad | " | 1,405 | " | weak-medium |
| Sharp | " | 1,300 | " | weak-medium |
| Broad | " | 1,150 | " | medium |
| Borad shoulder | " | 1,100 | " | weak |
| Sharp | " | 1,045 | " | medium-strong |
| Sharp shoulder | " | 915 | " | medium |
| Broad shoulder | " | 890 | " | weak |
| Broad shoulder | " | 760 | " | weak |

EXAMPLE 2

244 parts of a 78% strength aqueous solution of THPC (1 mol) and 51.5 parts (0.5 mol) of biuret are treated for 2 hours at 100°C internal temperature in a stirred vessel of 500 parts by volume capacity which is equipped with a thermometer and reflux condenser. Thereafter the mixture is cooled to room temperature and 291 parts of a yellow product of low viscosity are obtained. The active substance content is 76%.

The infrared spectrum of this product shows the following bands:

| | | | | |
|---|---|---|---|---|
| Broad | band at approx. | 3,240 | $cm^{-1}$ | strong |
| Broad shoulder | " | 2,980 | " | weak |
| Broad shoulder | " | 2,920 | " | weak |
| Broad shoulder | " | 2,860 | " | weak-medium |
| Broad shoulder | " | 2,650 | " | weak-medium |
| Broad shoulder | " | 2,480 | " | weak |
| Broad shoulder | " | 2,370 | " | weak |
| Broad | " | 2,080 | " | weak |
| Sharp shoulder | " | 1,740 | " | medium |
| Broad | " | 1,680 | " | medium-strong |
| Broad | " | 1,515 | " | medium |
| Broad | " | 1,400 | " | weak-medium |
| Broad shoulder | " | 1,285 | " | weak-medium |
| Broad | " | 1,230 | " | medium |
| Broad shoulder | " | 1,105 | " | weak |
| Sharp | " | 1,040 | " | medium-strong |
| Broad shoulder | " | 985 | " | weak |
| Sharp shoulder | " | 910 | " | medium |
| Broad shoulder | " | 885 | " | weak |
| Sharp | " | 760 | " | weak |

EXAMPLE 3

244 parts (1 mol) of a 78% strength aqueous THPC solution are cooled to 10°C in a stirred vessel of 500 parts by volume capacity, which is equipped with a reflux condenser and thermometer, and are neutralised to pH 7.2 with 55.5 parts of a 30% strength aqueous sodium hydroxide solution whilst stirring rapidly and cooling with ice. Thereafter 51.5 parts of biuret (0.5 mol) are added and condensation is carried out for 2 hours at 100° – 110°C. After cooling, 341.5 parts of a clear, colourless solution of low viscosity are obtained, of which the analysis shows a phosphorus content of 9.1%. The infrared spectrum of this product shows the following bands:

| | | | | |
|---|---|---|---|---|
| Broad | band at approx. | 3,300 | $cm^{-1}$ | strong |
| Broad shoulder | " | 3,000 | " | weak |
| Broad shoulder | " | 2,925 | " | weak |
| Broad shoulder | " | 2,860 | " | weak-medium |
| Broad shoulder | " | 2,670 | " | weak-medium |
| Broad shoulder | " | 2,480 | " | weak |
| Broad shoulder | " | 2,360 | " | weak |
| Broad | " | 2,080 | " | weak |
| Sharp shoulder | " | 1,725 | " | medium-strong |
| Broad | " | 1,680 | " | medium-strong |
| Broad | " | 1,525 | " | medium |
| Broad | " | 1,410 | " | weak-medium |
| Broad shoulder | " | 1,300 | " | weak-medium |
| Broad | " | 1,235 | " | medium |
| Broad shoulder | " | 1,165 | " | weak |
| Sharp | " | 1,045 | " | medium-weak |
| Broad | " | 895 | " | medium |
| Broad shoulder | " | 760 | " | weak |

EXAMPLE 4

244 parts (1 mol) of a 78% strength aqueous THPC solution are cooled to 10°C in a stirred vessel of 500 parts by volume capacity which is equipped with a reflux condenser and thermometer, and are neutralised to pH 7.2 with 67.5 parts of a 30% strength sodium hydroxide solution whilst stirring rapidly and cooling with ice. Thereafter 19 parts (0.25 mol) of thiourea are added and condensation is carried out for 30 minutes at 100° – 110°C. After cooling, 330 parts of a colourless, clear solution of low viscosity are obtained, the analysis of which shows a phosphorus content of 9.4%. The infrared spectrum of this product shows the following bands:

| | | | | |
|---|---|---|---|---|
| Broad | band at approx. | 3,260 | $cm^{-1}$ | strong |
| Broad shoulder | " | 2,970 | " | weak |
| Sharp | " | 2,910 | " | weak |
| Broad shoulder | " | 2,850 | " | medium |
| Broad shoulder | " | 2,650 | " | weak-medium |
| Broad shoulder | " | 2,470 | " | weak |
| Broad shoulder | " | 2,350 | " | weak |
| Broad | " | 2,070 | " | weak |
| Broad | " | 1,625 | " | medium |
| Broad | " | 1,535 | " | medium |
| Broad | " | 1,415 | " | medium |
| Broad shoulder | " | 1,365 | " | weak |
| Broad | " | 1,295 | " | weak |
| Broad | " | 1,190 | " | weak-medium |
| Broad shoulder | " | 1,100 | " | weak |
| Sharp | " | 1,040 | " | medium-strong |
| Broad shoulder | " | 1,015 | " | medium-strong |
| Broad shoulder | " | 920 | " | medium |
| Broad shoulder | " | 880 | " | weak-medium |
| Broad shoulder | " | 805 | weak | |

EXAMPLE 5

244 parts (1 mol) of a 78% strength aqueous solution of THPC, 19 parts (0.25 mol) of thiourea and 21.2 parts (0.25 mol) of a 35.4% strength aqueous formaldehyde solution are condensed for 2 hours at 100° – 105°C in a stirred vessel of 500 parts by volume capacity which is equipped with a reflux condenser and thermometer. After cooling, 276 parts of a colourless aqueous solution of the condensation product are obtained, the analysis of which shows a phosphorus content of 11.2%. The infrared spectrum of this product shows the following bands:

| | | | | |
|---|---|---|---|---|
| Broad | band at approx. | 3,260 | $cm^{-1}$ | strong |
| Broad shoulder | " | 2,980 | " | weak |
| Sharp | " | 2,920 | " | weak |
| Broad shoulder | " | 2,850 | " | weak-medium |
| Broad shoulder | " | 2,650 | " | weak-medium |
| Broad shoulder | " | 2,470 | " | weak |
| Broad shoulder | " | 2,350 | " | weak |
| Broad | " | 2,070 | " | weak |
| Broad | " | 1,635 | " | medium |
| Broad | " | 1,540 | " | medium |
| Broad | " | 1,420 | " | medium |
| Broad shoulder | " | 1,360 | " | weak |
| Broad shoulder | " | 1,300 | " | weak |
| Broad shoulder | " | 1,275 | " | weak |
| Broad | " | 1,205 | " | weak |

-continued

| | | | | |
|---|---|---|---|---|
| Broad shoulder | " | 1,110 | " | weak |
| Sharp | " | 1,045 | " | strong |
| Broad shoulder | " | 920 | " | medium |
| Broad shoulder | " | 880 | " | weak |
| Broad shoulder | " | 810 | " | weak |

-continued

| | | | | |
|---|---|---|---|---|
| Broad | " | 1,040 | " | medium-strong |
| Broad shoulder | " | 910 | " | medium |
| Broad shoulder | " | 880 | " | weak |
| Broad shoulder | " | 810 | " | weak |

EXAMPLE 6

244 parts (1 mol) of a 78% strength aqueous THPC solution and 90.5 parts (0.25 mol) of a 45% strength aqueous solution of the dimethylol compound of biuret are condensed for 2 hours at 100° – 105°C in a stirred vessel of 500 parts by volume capacity which is equipped with a reflux condenser and thermometer. After cooling, a yellowish solution, of low viscosity, of the condensation product is obtained, the analysis of which shows a phosphorus content of 9.65%. The infrared spectrum of this product shows the following bands:

| | | | | |
|---|---|---|---|---|
| Broad | band at approx. | 3,240 cm$^{-1}$ | strong |
| Broad shoulder | " | 2,970 | " | weak |
| Sharp | " | 2,910 | " | weak |
| Broad shoulder | " | 2,850 | " | medium |
| Broad shoulder | " | 2,630 | " | weak-medium |
| Broad shoulder | " | 2,470 | " | weak |
| Broad shoulder | " | 2,350 | " | weak |
| Broad | " | 2,070 | " | weak |
| Braod | " | 1,680 | " | strong |
| Broad shoulder | " | 1,645 | " | weak-medium |
| Broad | " | 1,520 | " | medium |
| Broad | " | 1,410 | " | medium |
| Broad shoulder | " | 1,295 | " | weak-medium |
| Broad | " | 1,230 | " | medium |
| Sharp | " | 1,110 | " | weak |
| Broad | " | 1,040 | " | medium-strong |
| Broad shoulder | " | 910 | " | medium |
| Broad shoulder | " | 880 | " | weak-medium |
| Broad shoulder | " | 815 | " | weak |
| Broad shoulder | " | 765 | " | weak |

EXAMPLE 7

244 parts (1 mol) of a 78% strength aqueous solution of THPC and 26.5 parts (0.25 mol) of the monomethylol compound of thiourea are condensed for 2 hours at 100° – 105°C in a stirred vessel of 500 parts by volume capacity which is equipped with a reflux condenser and thermometer. After cooling, 267 parts of a colourless mobile solution of the condensation product are obtained, the analysis of which shows a phosphorus content of 11.6%. The infrared spectrum of this product shows the following bands:

| | | | | |
|---|---|---|---|---|
| Broad | band at approx. | 3,240 cm$^{-1}$ | strong |
| Broad shoulder | " | 2,970 | " | weak |
| Sharp | " | 2,910 | " | weak |
| Broad shoulder | " | 2,850 | " | medium |
| Broad shoulder | " | 2,630 | " | medium |
| Broad shoulder | " | 2,470 | " | weak |
| Broad shoulder | " | 2,350 | " | weak |
| Broad | " | 2,070 | " | weak |
| Broad | " | 1,630 | " | medium-strong |
| Broad | " | 1,535 | " | medium |
| Broad | " | 1,410 | " | medium |
| Broad shoulder | " | 1,350 | " | weak |
| Broad shoulder | " | 1,290 | " | weak |
| Broad shoulder | " | 1,275 | " | weak |
| Broad | " | 1,195 | " | weak |
| Broad | " | 1,105 | " | weak |

EXAMPLE 8

190.5 parts (1 mol) of anhydrous crystalline THPC and 1.52 parts (0.02 mol) of thiourea are condensed in the melt for 2 hours at 100° – 105°C in a stirred vessel of 500 parts by volume capacity which is equipped with a reflux condenser and thermometer. Thereafter the mixture is cooled to 50°C, 80 parts of methanol and 0.1 part of aqueous 37% strength hydrochloric acid are added and the mixture is etherified for 30 minutes at 65°C (reflux temperature). The excess methanol is subsequently removed in vacuo at 50°C. 186.5 parts of a highly viscous reddish-coloured condensation product are obtained, the analysis of which shows a phosphorus content of 16.6%. The infrared spectrum of the product shows the following bands:

| | | | | |
|---|---|---|---|---|
| Broad | band at approx. | 3,240 cm$^{-1}$ | strong |
| Broad shoulder | " | 2,970 | " | weak |
| Sharp | " | 2,920 | " | weak |
| Broad shoulder | " | 2,850 | " | medium |
| Broad shoulder | " | 2,640 | " | weak-medium |
| Broad shoulder | " | 2,470 | " | weak |
| Broad shoulder | " | 2,350 | " | weak |
| Broad | " | 2,070 | " | weak |
| Broad | " | 1,630 | " | medium-strong |
| Broad | " | 1,520 | " | weak |
| Broad | " | 1,415 | " | medium |
| Broad | " | 1,295 | " | weak |
| Broad | " | 1,190 | " | weak |
| Broad shoulder | " | 1,110 | " | weak |
| Sharp | " | 1,040 | " | medium-strong |
| Broad shoulder | " | 915 | " | medium |
| Broad shoulder | " | 880 | " | weak |
| Broad shoulder | " | 810 | " | weak |

EXAMPLE 9

Mixed fabrics of polyester-cotton (PES/CO), 50:50 and 67:33, are padded with the liquors according to Table 1 below, dried for 30 minutes at about 80°C and subsequently cured for 5 minutes at 150°C (thermofixing process).

The fabrics are then washed for 5 minutes at 60°C in a liquor which per litre contains 5 ml of hydrogen peroxide (35% strength), 3 g of aqueous sodium hydroxide solution (30% strength) and 1 g of a 25% strength aqueous solution of a condensation product of 1 mol of p-tert.-nonylphenol and 9 mols of ethylene oxide. Thereafter the fabrics are rinsed and dried. The degree of fixing indicates the amount of product present on the fibre material after rinsing (relative to the amount originally absorbed).

The fabrics are then washed up to 40 times for 45 minutes at 60°C in a domestic washing machine, in a liquor which contains 4 g/l of a domestic detergent (SNV 198.861 wash). The individual fabric samples are then tested for their flameproof character (DIN 53,906 vertical test; ignition time 6 seconds). Untreated fabrics burn away.

The results are also summarised in Table 1 below.

Table 1

| Constituents g/l | Treated with liquor (thermofixing process) | | |
|---|---|---|---|
| | A 50:50 | B 67:33 | C 67:33 |
| Product according to Example 1 | 455 | 455 | — |
| Product according to Example 2 | — | — | 725 |
| Dimethylolmelamine | 96.5 | 96.5 | 96.5 |
| pH value of the liquor (adjusted with NaOH) | 5.5 | 5.5 | 5.5 |
| Liquor uptake, % | 75 | 75 | 70 |
| Phosphorus content per kg of fabric, g | 52 | 52 | 56 |
| Degree of fixing, % | 77 | 83 | 66 |
| Flameproof character | | | |
| After rinsing | | | |
| Smouldering time (seconds) | 0 | 0 | 0 |
| Tear length (cm) | 10 | 11.5 | 12.5 |
| After 20 washes (60°C) | | | |
| Smouldering time (seconds) | 0 | 0 | 0 |
| Tear length (cm) | 10 | 9.5 | 11.5 |
| After 40 washes (60°C) | | | |
| Smouldering time (seconds) | 0 | 0 | 0 |
| Tear length (cm) | 8.5 | 10 | 12 |

EXAMPLE 10

A polyester (PES) fabric is padded with the liquor of Table 2 below, dried for 30 minutes at about 80°C and subsequently cured for 5 minutes at 150°C (thermofixing process).

The polyester fabric is then washed for 5 minutes at 40°C in a liquor which per litre contains 4 g of sodium carbonate and 1 g of a 25% strength aqueous solution of a condensation product of 1 mol of p-tert.-nonylphenol and 9 mols of ethylene oxide. Thereafter the fabric is rinsed and dried.

The degree of fixing indicates the amount of the flameproofing agent after rinsing, in per cent of the original amount taken up.

The fabric is then tested for its flameproof character. The results are also summarised in Table 2 below.

Table 2

| Constituents g/l | Untreated | Treated with liquor |
|---|---|---|
| Product according to Example 2 | | 765 |
| Dimethylolmelamine | | 120 |
| pH value of the liquor (adjusted with NaOH) | | 5.5 |
| g/l of phosphorus | | 84 |
| Liquor uptake, % | | 70 |
| Degree of fixing, % | | 77 |
| Flameproof character | | |
| After condensing | burns | |
| Smouldering time (seconds) | | 5 |
| Tear length (cm) | | 12.5 |
| After rinsing | | |
| Smouldering time (seconds) | | 4 |
| Tear length (cm) | burns | 13 |

EXAMPLE 11

Mixed fabrics of polyester-cotton (PES/CO), 50:50 and 67:33, cotton serge (CO) and wool gaberdine (W) are padded with the liquors according to Table 3 below, dried for 30 minutes at about 80°C and subsequently cured for 5 minutes at 150°C (thermofixing process).

The polyester-cotton (PES/CO) mixed fabrics are then washed for 5 minutes at 60°C in a liquor which per liter contains 5 ml of hydrogen peroxide (35%), 3 g of aqueous sodium hydroxide solution (30%) and 1 g of a 35% strength aqueous solution of a condensation product of 1 mol of p-tert.-nonylphenol and 5 moles of ethylene oxide. Thereafter the fabric is rinsed and dried.

The cotton fabric (CO) is washed for 5 minutes at 95°C and the wool fabric (W) is washed for 5 minutes at 40°C, in a liquor which per liter contains 4 g of sodium carbonate and 1 g of a 25% strength solution of a condensation product of 1 mol of p-tert.-nonylphenol and 9 mols of ethylene oxide. Thereafter the fabric is rinsed and dried.

In addition to the thermofixing process (T) just described, the fabrics are in part also finished by the ammonia fixing process (A) or by the moist batch process (M).

In the case of the ammonia fixing process (A), the padded polyester-cotton mixed fabric (PES/CO), 50:50 and 67:33, is dried at 80°C (not completely), treated for 10 minutes with ammonia gas, and then treated for 10 minutes with a liquor which contains 300 ml of a 24% strength aqueous ammonia solution per liter. Thereafter the fabric is washed for 10 minutes at 40°C in a liquor which per liter contains 6 ml of hydrogen peroxide (35% strength) and 5 g of soap. It is then rinsed and dried.

In the case of the moist batch process (M) the padded polyester-cotton mixed fabric (PES/CO), 50:50 and 67:33, is dried to 10% residual moisture, packed in a plastic film, batched for 24 hours at 50°C and then rinsed. Thereafter the fabric is washed for 5 minutes at 40°C in a liquor which per liter contains 4 g of sodium carbonate and 1 g of a 25% strength aqueous solution of a condensation product of 1 mol of p-tert.-nonylphenol and 5 mols of ethylene oxide. Thereafter the fabric is rinsed and dried.

The degree of fixing indicates the amount of product present on the fibre material after rinsing (relative to the amount originally taken up).

The fabrics treated in accordance with the 3 processes described above are then washed up to 20 times for 45 minutes at 40°C(W), 60°C (PES/CO) or 95°C (CO) in a domestic washing machine, in a liquor which contains 4 g/l of a domestic detergent (SNV 198,861 wash). The individual fabric samples are then tested for their flameproof character (DIN 53,906 vertical test, ignition time 6 seconds). Untreated fabrics burn away.

The results are also summarised in Table 3 below.

Table 3

| Fabric | PES/CO 50:50 | PES/CO 67:33 | PES/CO 50:50 | PES/CO 50:50 | PES/CO 67:33 | PES/CO 50:50 | PES/CO 50:50 | 67:33 | W | PES/CO 50:50 | PES/CO 67:33 | PES/CO 50:50 | PES/CO 67:33 | PES/CO 50:50 | PES/CO 50:50 |
|---|---|---|---|---|---|---|---|---|---|---|---|---|---|---|---|
| Process | T | T | T | T | T | M | T | T | T | T | T | T | T | T | A |
| Constituents in g/l | | | | | | | | | | | | | | | |
| Product according to Example 3 | 895 | 895 | | | | | | | | | | | | | |
| Product according to Example 4 | | | 865 | | | | | | | | | | | | |
| Product according to Example 5 | | | | 730 | 730 | 730 | | | | | | | | | |
| Product according to Example 6 | | | | | | | 845 | 845 | 695 | 455 | | | | | |
| Product according to Example 7 | | | | | | | | | | | 705 | 705 | 705 | 705 | | |
| Product according to Example 8 | | | | | | | | | | | | | | | 490 | 490 |
| Di-trimethylol-melamine | 103 | 103 | 103 | 103 | 103 | 103 | 103 | 103 | 84.5 | 120 | 103 | 103 | 103 | 103 | | |
| Trimethylolmelamine-dimethyl-ether (75% strength) | | | | | | | | | | | | | | | 153 | 153 |
| Constituents in g/l | | | | | | | | | | | | | | | |
| Condensation product of 1 mol of p-tert.-nonylphenol and 9 mols of ethylene oxide | | | | | | | | | 2 | | | | | | | |
| Silicone oil emulsion (40% strength) | | | 35 | 35 | 35 | 35 | 35 | 35 | 35 | 35 | 35 | 35 | 35 | 35 | 35 | 35 |
| pH value of the liquor (adjusted with NaOH) | 7* | 7* | 4.5 | 4.5 | 4.5 | 4.5 | 4.5 | 4.5 | 4.5 | 4.5 | 4.5 | 4.5 | 7* | 7* | 4.5 | 4.5 |
| Phosphorus content per kg of fabric | 57 | 57 | 57 | 57 | 57 | 57 | 57 | 57 | 67 | 35 | | | | | | |
| Degree of fixing, % | 81 | 83 | 74 | 81 | 81 | — | 80 | 83 | 23 | 52 | | | | | | |
| Flameproof character | | | | | | | | | | | | | | | | |
| After rinsing | | | | | | | | | | | | | | | | |
| Smouldering time (seconds) | 0 | 0 | 0 | 0 | 0 | 0 | 0 | 0 | 2 | 0 | | | | | | |
| Tear length (cm) | 8.5 | 11 | 9.5 | 9.5 | 13 | 12 | 9 | 9 | 7.5 | 8.5 | | | | | | |
| After 20 washes | | | | | | | | | | | | | | | | |
| Smouldering time (seconds) | 0 | 0 | 0 | 0 | 0 | 0 | 0 | 0 | 12 | 0 | | | | | | |
| Tear length (cm) | 8 | 8 | 7 | 12 | 8 | 7 | 9.5 | 10 | 12 | 8.5 | | | | | | |

Table 3-continued

| Fabric | PES/CO 50:50 | PES/CO 67:33 | PES/CO 50:50 | PES/CO 67:33 | PES/CO 50:50 | PES/CO 50:50 |
|---|---|---|---|---|---|---|
| Process | T | T | T | T | T | A |
| Phosphorus content per kg of fabric | 57 | 57 | 57 | 57 | 57 | 57 |
| Degree of fixing, % | 89 | 93 | 79 | 95 | 57 | — |
| Flameproof character After rinsing | | | | | | |
| Smouldering time (seconds) | 0 | 0 | 0 | 0 | 0 | 0 |
| Tear length (cm) | 7.5 | 12 | 7.5 | 10 | 8 | 7 |
| After 20 washes | | | | | | |
| Smouldering time (seconds) | 0 | 3 | 0 | 0 | 3 | 0 |
| Tear length (cm) | 9.5 | 10 | 7 | 12 | 7.5 | 6 |

*Product converted to the hydroxyl compound

EXAMPLE 12

The mixed fabric of polyester-cotton (PES/CO), 67:33, is padded with the liquors according to Table 4 below, dried for 30 minutes at about 80°C and subsequently cured for 5 minutes at 150°C (thermofixing process).

The polyester-cotton mixed fabric is then washed in accordance with the instructions of Example 11. The degree of fixing indicates the amount of product present on the fibre material after rinsing (relative to the amount originally absorbed).

The treated fabric is then washed up to 5 times, following the procedure in Example 11. The individual fabric samples are then tested for their flameproof character (DIN 53,906 vertical test, ignition time 6 seconds). Untreated fabrics burn away.

The results are also summarised in Table 4 below.

Table 4

| Fabric | PES/CO 67:33 | PES/CO 67/33 |
|---|---|---|
| Process | T | T |
| Constituents in g/l | | |
| Product according to Example 4 | 865 | |
| " 8 | | 490 |
| Di-trimethylolmelamine | 103 | |
| Trimethylolmelamine-dimethyl-ether (75% strength) | | 153 |
| Silicone oil emulsion (40% strength) | | 35 |
| pH value of the liquor (adjusted with NaOH) | 4.5 | 4.5 |
| Phosphorus content per kg of fabric | 57 | 57 |
| Degree of fixing, % | 83 | 62 |
| Flameproof character After rinsing | | |
| Smouldering time (seconds) | 0 | 2 |
| Tear length (cm) | 11 | 10 |
| After 5 washes | | |
| Smouldering time (seconds) | 0 | 3 |
| Tear length (cm) | 12 | 12 |

EXAMPLE 13

The padded polyester-cotton mixed fabric (PES/CO), 67:33, is dried at 50°C (not completely), treated with ammonia gas for 10 minutes, and then treated for 10 minutes with a liquor which contains 300 ml of a 24% strength aqueous ammonia solution per liter (ammonia fixing process). Thereafter the fabric is washed in accordance with the instructions of Example 11.

Apart from the ammonia fixing process (A) described above, it is also possible to use the moist batch process (M).

In the moist batch process (M), the padded polyester-cotton mixed fabric (PES/CO), 67:33, is dried to 10% residual moisture, packed in a plastic film, stored for 24 hours at 50°C and then rinsed. Thereafter the fabric is washed as described in Example 11.

The fabrics treated in accordance with the 2 processes described above are then washed, following the instructions of Example 11. The individual fabric samples are then tested for their flameproof character (DIN 53,906 vertical test, ignition time 6 seconds). Untreated fabrics burn away.

The results are summarised in Table 5 below.

Table 5

| Fabric | PES/CO 67:33 | PES/CO 67:33 |
|---|---|---|
| Process | F | A |
| Constituents in g/l | | |
| Product according to Example 5 | 730 | |
| " 8 | | 490 |
| Di-trimethylolmelamine | 103 | |
| Trimethylolmelaminedimethyl-ether (75% strength) | | 153 |
| pH value of the liquor (adjusted with NaOH) | 4.5 | 4.5 |
| Phosphorus content per kg of fabric | 57 | 57 |
| Flameproof character After rinsing | | |
| Smouldering time (seconds) | 9 | 0 |
| Tear length (cm) | 11 | 10 |
| After one wash | | |
| Smouldering time (seconds) | 14 | 0 |
| Tear length (cm) | 10 | 12 |

We claim:

1. A process for the manufacture of a water-soluble condensation product of a hydroxymethyl-phosphonium compound and biuret, wherein 1 mol of a tetrakis-(hydroxymethyl)-phosphonium halide or tetrakis-(hydroxymethyl)-phosphonium hydroxide is mixed and heated at 40°C to 120°C with 0.02 to 0.5 mols of biuret.

2. Condensation products of one mol of tetrakis-(hydroxymethyl)-phosphonium hydroxide or a tetrakis-(hydroxymethyl)-phosphonium halide and 0.02 to 0.5 mols of methylolated or non methylolated biuret condensed at 40° to 120°C.

3. Condensation products according to claim 2 of one mol of tetrakis-(hydroxymethyl)-phosphonium hydroxide or a tetrakis-(hydroxymethyl)-phosphonium halide and 0.1 to 0.3 mols of methylolated or non methylolated biuret condensed at 40° to 120°C.

4. Condensation products according to claim 2, further condensed at 100° to 150°C.

5. Condensation products according to claim 2 condensed in the melt.

6. Condensation products according to claim 2 condensed in water.

7. Condensation products according to claim 2 condensed in an inert organic solvent.

8. Condensation products according to claim 2 condensed in an inert aromatic hydrocarbon as the solvent.

9. Condensation products according to claim 2 of non methylolated biuret.

10. A process for the manufacture of a water-soluble condensation product of a hydroxymethyl-phosphonium halide and biuret, wherein one mol of a tetrakis-(hydroxymethyl)-phosphonium halide is mixed and heated at 40° to 120°C with 0.02 to 0.5 mols of biuret.

11. Process according to claim 10, characterised in that the condensation is carried out in the presence of at least one inert aromatic hydrocarbon as the solvent.

12. Process according to claim 10, characterised in that the two starting materials are condensed with one another in a molar ratio of 1:0.1 to 1:0.3.

* * * * *